US00PP15955P3

(12) United States Plant Patent
Zary

(10) Patent No.: US PP15,955 P3
(45) Date of Patent: Sep. 13, 2005

(54) HYBRID TEA ROSE PLANT NAMED 'ZARYELLOW'

(50) Latin Name: *Rosa hybrida*
Varietal Denomination: Zaryellow

(75) Inventor: Keith Zary, Somis, CA (US)

(73) Assignee: E.G. Hill Company Inc., Richmond, IN (US)

( * ) Notice: Subject to any disclaimer, the term of this patent is extended or adjusted under 35 U.S.C. 154(b) by 0 days.

(21) Appl. No.: 10/377,336

(22) Filed: Feb. 28, 2003

(65) Prior Publication Data

US 2004/0172731 P1 Sep. 2, 2004

(51) Int. Cl.[7] ..... A01H 5/00
(52) U.S. Cl. ..... Plt./134
(58) Field of Search ..... Plt./134, 130

*Primary Examiner*—Anne Marie Grunberg
*Assistant Examiner*—June Hwu
(74) *Attorney, Agent, or Firm*—Christie, Parker & Hale, LLP

(57) ABSTRACT

A hybrid tea rose plant variety producing large yellow flowers.

1 Drawing Sheet

Classification: *Rosa hybrida.*
Varietal designation: 'Zaryellow'.

BACKGROUND OF THE INVENTION

The present invention relates to a new and distinct hybrid tea rose variety which was originated by crossing as seed parent the variety known as 'JACyem' (U.S. Plant Pat. No. 9,329) and as the pollen parent the variety known as '79-0004511' (non-patented). The varietal denomination of this new rose is 'Zaryellow'.

SUMMARY OF THE INVENTION

Among the novel characteristics possessed by the new variety which distinguish it from its parents and all other varieties of which I am aware is its stable deep yellow color and larger head size.

Asexual reproduction by budding of the new variety as performed in Somis, Calif., shows that the foregoing and other distinguishing characteristics come true to form and are established and transmitted through succeeding propagations. Other known forms of asexual reproduction may be used also.

COMPARISON WITH PARENTS

'Zaryellow' has a deeper color than its seed parent and the color is stable throughout opening. The head size of 'Zaryellow' is much larger than the head size of the pollen parent.

DISTINCTION FROM SIMILAR RELATED CULTIVARS

'Zaryellow' as compared to Gold Strike has longer peduncles and longer stems. 'Zaryellow' has longer stems and a deeper, more golden color than Skyline.

BRIEF DESCRIPTION OF ILLUSTRATION

The accompanying illustration shows typical specimens of the vegetative growth and flowers of the new variety in different stages of development and depicted in color as nearly true as it is reasonably possible to make the same in a color illustration of this character.

DESCRIPTION OF THE NEW VARIETY

The following is a detailed description of the new variety, from specimens grown under glass in Richmond, Ind., in the month of January. The age of the observed plant is 2 years. The color terminology used is in accordance with The Royal Horticultural Society Colour Chart (R.H.S.C.C.), and refers to plate numbers in the aforementioned color chart. Phenotypic expression may vary depending on light, environmental and cultural conditions.

Bud:

*Peduncle.*—About 5¼ inch in length, and erect with entirely smooth bark.
*Color.*—Near 144A.
*Thorns.*—None.
*Prickles.*—None.
*Hairs.*—None.
*Before calyx breaks.*—Bud size: Medium small, about ¾ inch in length. Bud form: Short pointed without a conspicuous neck; with foliaceous appendages on the surface of the bud, with slender foliaceous parts extending beyond the tip of the bud equal to about ½ or more its length. Color of calyx: Near 144A, funnel shaped, some have a margin fringed ranging from 1/16 to ¼ inches in length with hairs and small appendages.
*As calyx breaks.*—Color near 17B shaded with 14C; base of petal near 145A.
*As first petal breaks.*—Bud size: Medium large, 1 to 2 inches in length. Bud form: Obtuse. Color of petal: Outside: Near 13B. Inside: Near 14B.
*Bud opening in greenhouse.*—Bud opens well.

Flower:

*Flowers borne.*—One per stem, on strong stems, 22–30 inches in length.
*Continuity in greenhouse.*—Continuous.
*Fragrance in greenhouse.*—Slight musk.

*Bloom* (*open*).—Size when fully open: About 4½ inches to 5 inches.
*Petalage.*—Double, 28 to 32 petals per bloom.
*Form.*—At first high centered, becoming flat, remaining rolled outward at first; petals loosely roll outward at maturity.
*Petals.*—Moderately thick, inside satiny, outside satiny.
*Petals/shape.*—Outside petals: Elliptic; apex mucronate. Intermediate petals: Elliptic; apex mucronate. Inside petals: Elliptic; apex mucronate. Average petal size: 1⅝ inches across and 1⅞ inches in length. Petal margin type: Entire.

The following description is of a newly opened flower from a rose grown in a greenhouse.

*Color of outer petal.*—Outside surface: Near 17B. Inside surface: Near 14A.
*Color of intermediate petal.*—Outside surface: Near 21B; base near 14B. Inside surface: Near 14B.
*Color of inner petal.*—Outside surface: Near 21B; base near 14B. Inside surface: Near 14A.
*Behavior of petals in greenhouse.*—Persist.
*Flower longevity.*—About 7 days in February after cutting.
*Color of open bloom.*—Near 14A.
*Color three days open.*—Near 14A.

The following description was made from a rose that was open for three days in a greenhouse.

*Color of outer petal.*—Outside surface: Near 13B. Inside surface: Near 13B, shaded to near 13A.
*Color of intermediate petal.*—Outside surface: Near 15A. Inside surface: Near 14A.
*Color of inner petal.*—Outside surface: Near 16A. Inside surface: Near 13A.

Foliage:
*Leaves.*—Length of leaf — approximately 5–7 inches; width of leaf — approximately 4 inches; leathery.
*Leaflets.*—Shape: Elliptical. Apex: Acute.
*Base.*—Elliptical.
*Margin.*—Simply serrate.
*Color of leaflets.*—Mature, upper surface: Near 137A. Mature, under surface: Near 138B. Young, upper surface: Near 138A bordered 187A. Young, under surface: Near 181A shaded 181B.
*Rachis.*—Upper side: Smooth, grooved, with few hairs on the edges of the groves. Under side: Smooth, some have a few small thorns.
*Stipules.*—Medium length ½ to ¾ inch, medium width 3/16 to ¼ inch with points which are medium length 3/16 turning out at an angle of more than 45 degrees, color near 144A.

Growth:
*Height.*—Approximately 5'6".
*Spread.*—Approximately 2'.
*Habit.*—Bush, upright, branched.
*Growth.*—Moderately vigorous.
*Canes.*—Medium diameter.
*Main stems.*—Near 146B. Thorns: Several, medium length (about ¼ to 7/16 inches), straight, with narrow base. Color of thorns: Near 166A shaded with 166B. Prickles: None. Hairs: None. Branches: Near 146A in color. Color of thorns: Near 146B, shaded to near 146C.
*New shoots.*—Color: Near 184B shaded with 138B. Thorns: Few, medium length (3/16 inch to 5/16 inch), straight with narrow base. Color of thorns: Near 46A; tip near 146C. Prickles: None. Hairs: None.

Reproductive organs:
*Stamens.*—Medium number (approximately 10), arranged regularly about pistils.
*Filaments.*—Short, approximately 3/16 inch to ½ inch in length, most with anthers.
*Color of filaments.*—Near 15A some with a base color 45B.
*Color of anthers.*—Near 21A shaded 21B.
*Pollen.*—Moderate.
*Color of pollen.*—Near 162C.
*Pistils.*—Many (Approx. 103).
*Styles.*—Short, medium length (1/18 inch to ¼ inches in length), moderately thin, bunched.
*Color of styles.*—Near 3D.
*Color of stigma.*—Near 16B.
*Ovularies.*—All encased in calyx.
*Hips.*—N/A.
*Sepals.*—Permanent, medium, straight, funnel shaped; some have a margin fringed with hairs and appendages of about 1/16 to ¼ inch long, color near 144A. Under side: Near 143A; base 144C. Upper side: Near 138A; base near 138C.
*Seeds.*—N/A.

I claim:

1. A new and distinct hybrid tea rose plant of the variety substantially as shown and described.

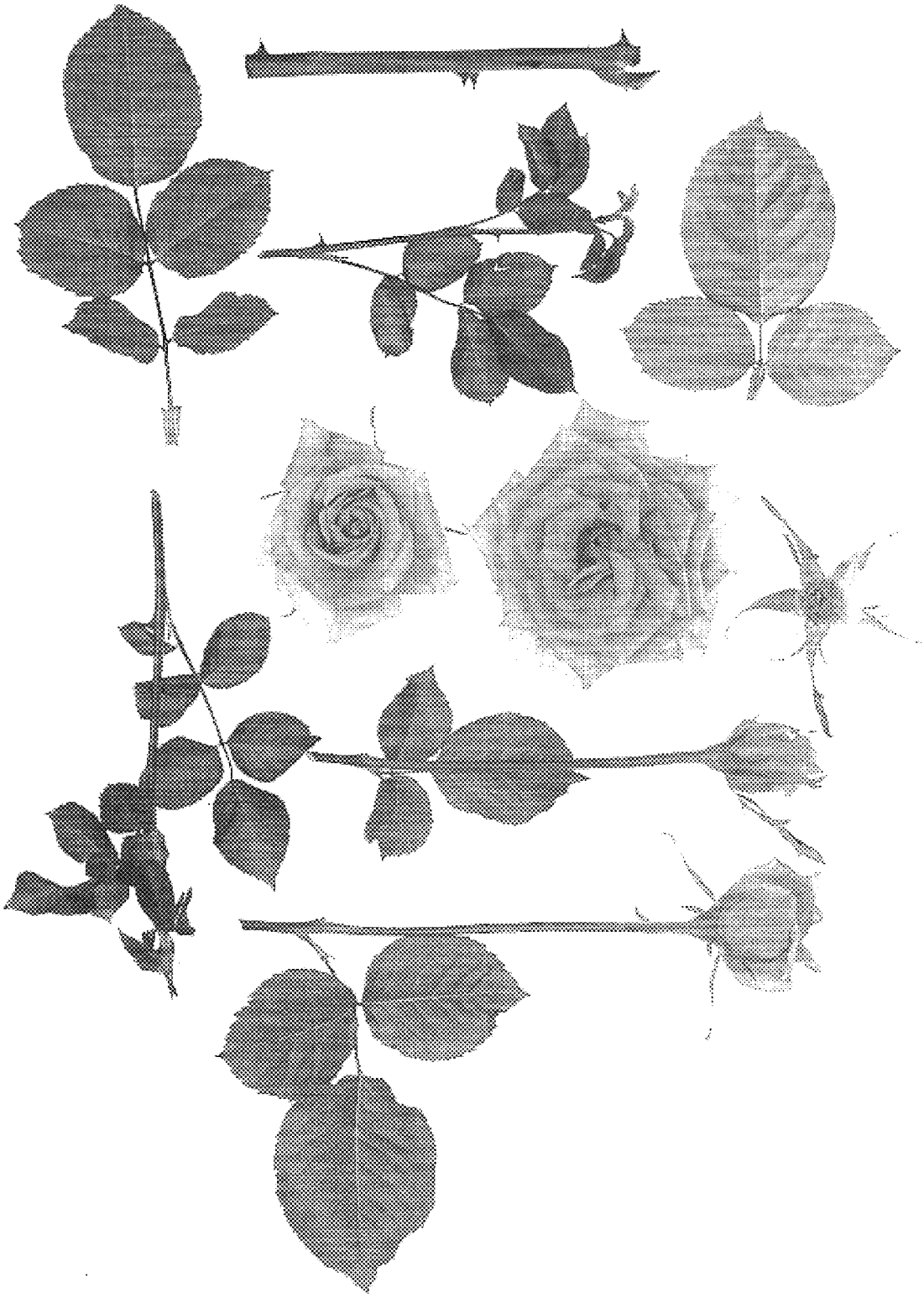

* * * * *